United States Patent [19]

Farber

[11] 4,020,056
[45] Apr. 26, 1977

[54] DI-VINYL PHTHALIDES COLOR FORMERS

[75] Inventor: Sheldon Farber, Appleton, Wis.

[73] Assignee: NCR Corporation, Dayton, Ohio

[22] Filed: Apr. 10, 1975

[21] Appl. No.: 566,851

[52] U.S. Cl. .................. 260/240 D; 260/343.2 F; 260/343.3 R

[51] Int. Cl.$^2$ ..................................... C07D 307/88

[58] Field of Search ............ 260/343.3 R, 343.2 R, 260/240 D, 343.2 F

[56] References Cited

UNITED STATES PATENTS

| | | | |
|---|---|---|---|
| 3,677,752 | 7/1972 | Looker et al. | 96/1.6 |
| 3,703,397 | 11/1972 | Chao-Han Lin et al. | 117/36.2 |
| 3,736,337 | 5/1973 | Farber | 260/343.3 |
| 3,825,561 | 7/1974 | Akamatsu et al. | 260/335 |
| 3,884,506 | 5/1975 | Ozutsumi et al. | 282/27.5 |
| 3,928,685 | 12/1975 | Alsop | 428/411 |
| 3,930,108 | 12/1975 | Alsop | 428/411 |

OTHER PUBLICATIONS

Lorenz and Wizinger, Helv. Chim. Acta., vol. 28, pp. 600–612, (1945).
Hallas, Journal of the Society of Dyers and Colorists, pp. 368–383, Sept. 1967; pp. 510–516, Oct. 1968; pp. 237–242, June 1970.
Zwanenburg et al., Recueil, J. of the Royal Netherlands Chemical Society, 94/1, 1/75, pp. 8–12, 94/9–10, pp. 215–218 & 218–220, Sept.–Oct. 1975.

*Primary Examiner*—Donald G. Daus
*Assistant Examiner*—Jose Tovar
*Attorney, Agent, or Firm*—E. Frank McKinney

[57] ABSTRACT

A chromogenic compound of normally colorless form is disclosed having the following structural formula:

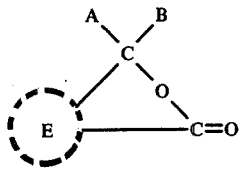

wherein A and B can be

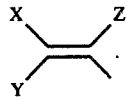

X, Y and Z can be, among several others, hydrogen, alkyl, alkoxy, aryl, and heterocyclic, substituted and unsubstituted; and E can be a broad family of aromatic and heterocyclic structures. The compound is eligible for use in pressure-sensitive record materials and manifold marking systems. Because of light absorption characteristics, selected compounds of this invention are especially useful where machine readability and machine copiability are important.

7 Claims, 3 Drawing Figures

(I)

(A)

(II)

(B)

(III)

DI-VINYL PHTHALIDES COLOR FORMERS

BACKGROUND OF THE INVENTION

1. Field of the Invention

This invention pertains to colorable chromogenic compounds eligible for use in pressure-sensitive record material. Pressure-sensitive mark-forming record systems, single sheet and manifold, are improved by use of these compounds.

More specifically, this invention relates to chromogenic compounds having two vinyl linkages which compounds have the form of substantially colorless or slightly colored solids, or which approach being colorless when in liquid solution; but, which may be converted to dark-colored forms upon reactive contact with acidic material. As used in mark-forming systems, marking in desired areas on support webs or sheets may be accomplished by effecting localized reactive contact between the chromogenic material and the acidic material on or in such web or sheet, such material being brought thereto by transfer or originally there, in situ;---the desired reactive contact forming dark-colored materials in the intended image-marking areas.

The chromogenic compounds of this invention have the following general formula:

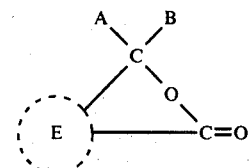

wherein A and B can be

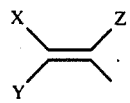

X, Y, and Z can be, among several others, hydrogen, alkyl, alkoxy, aryl, and heterocyclic, substituted and unsubstituted; and E can be a broad family of aromatic and heterocyclic structures.

The chromogenic compounds of this invention especially relate to marks at or near the near infrared part of the color spectrum; and, in that regard, especially relate to providing a color which is particularly visible to machine readers and copiers.

2. Description of the Prior Art

Several phthalide and fluoran chromogenic compounds have been disclosed. For example, U.S. Pat. Nos. 3,491,111, and 3,491,116, issued Jan. 20, 1970, disclose indol- and carbazol-substituted phthalides. U.S. Pat. No. 2,417,897, issued Mar. 25, 1947, discloses crystal violet lactone. U.S. Pat. No. 3,681,390 issued Aug. 1, 1972, discloses arylsubstituted fluorans.

U.S. Pat. No. 3,672,935, issued June 27, 1972, discloses use of colorless chromogenic compounds in pressure-sensitive record material.

G. Hallas, in the *Journal of the Society of Dyers and Colourists*, in September, 1967 at pages 368 to 373 and in June, 1970 at pages 237–242 discusses the effects of extended conjugation on colored dye compounds.

SUMMARY OF THE INVENTION

Colorable chromogenic compounds having two vinyl linkages have been discovered which compounds are initially substantially colorless but produce dark-colored products on reaction with certain acid materials. The vinyl-containing chromogenic compounds exhibit light absorption, in the colored form, at wavelengths nearer to infrared than chromogenic compounds without vinyl groups. It is an object of this invention to provide such vinyl-containing compounds and methods for making them.

An important use for the vinyl compounds of this invention resides in their incorporation into pressure-sensitive record systems as a colorable reactant for development of color on application of a mark-forming force. Hence, it is an object of this invention to provide substances having near infrared color response and chromogenic properties, which substances can be incorporated in a web or coated onto the surface of a web to provide a record sheet or a manifolding unit, and which are useful in carrying out methods of marking involving reactive contact with a color-activating material to develop dark-colored materials in areas where marking is desired.

It is an object of this invention to provide modified compounds, based upon the aforementioned vinyl-containing compounds, which are substantially colorless, or slightly colored, offering a variety of chromogenic characteristics, and developing dark-colored substances absorbing at increased wavelengths upon contact with color-activating materials.

BRIEF DESCRIPTION OF THE DRAWING

The chromogenic compounds of this invention include a large variety of several moieties, with the vinyl linkages and lactone rings being necessarily common to all. In order to more completely and more distinctly disclose the variety of moiety combinations which forms a part of this invention, a drawings is included which is a schematic representation of the combinations, by structural formula.

Also included as drawings, are graphic representations of the absorption spectra of compounds of this invention compared with the spectra of similar compounds from the prior art.

Figure 1:
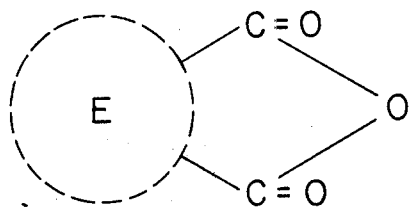
Figure 1:
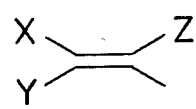
Figure 1:
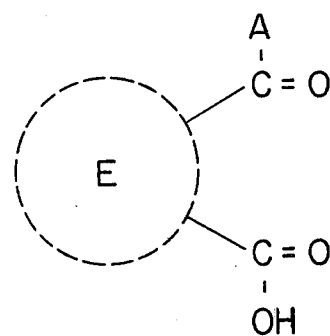
Figure 1:
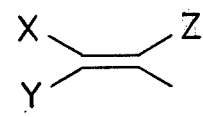
Figure 1:
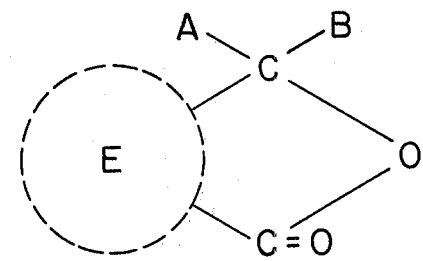

The drawing represents a figurative, schematic, step-by-step structural development of the vinyl-containing compounds of this invention, as they can be prepared. A dicarboxylic anhydride (I) is combined with a vinyl-containing substrate (A) to yield a keto acid (II), which is, in turn, combined with a vinyl-containing substrate reactant (B) to yield the chromogenic compound (III) of this invention. The structural development shown is not necessarily a representation of the actual compound synthesis. For example, in preparing divinyl compounds of this invention, the reaction does not necessarily go through separate and individual steps, as shown; and, in fact, the keto acid (II) may have only a fleeting existence, if it exists at all. The synthetic process is not embraced as a part of this invention.

The dicarboxylic anhydride (I), in FIG. 1, includes E as the supporting molecular structure. E represents a large variety of structures including aromatic and heterocyclic, substituted and unsubstituted. The substitutions include halo, nitro, cyano, and alkylthio, alkoxy, alkyl, monoalkylamino, and dialkylamino with alkyl of less than seven carbon atoms. Halogen or halo-, in this invention, means fluorine, chlorine, bromine and iodine. (I) is not required to be a dicarboxylic anhydride. A dicarboxylic acid will suffice if the keto acid-forming reaction is conducted under dehydrating conditions such as in acetic anhydride. Moreover, the vinyl-containing compounds (A) and (B) can be a methyl carbinol under dehydrating conditions.

Figuratively speaking and in accord with the drawing, substrate moieties are added to the supporting molecular structure and the substrate moieties must each contain a vinyl linkage.

(A) and (B) provide structural, schematic, indication of the manner in which vinyl linkages are introduced into the compounds of this invention. While there are differences between the specific moieties which will be disclosed in detail, below, it suffices to say, here, that X, Y, and Z represent, among other things, substituted and unsubstituted aromatic and heterocyclic groups as a part of the moieties of (A) and (B).

Figure 2:
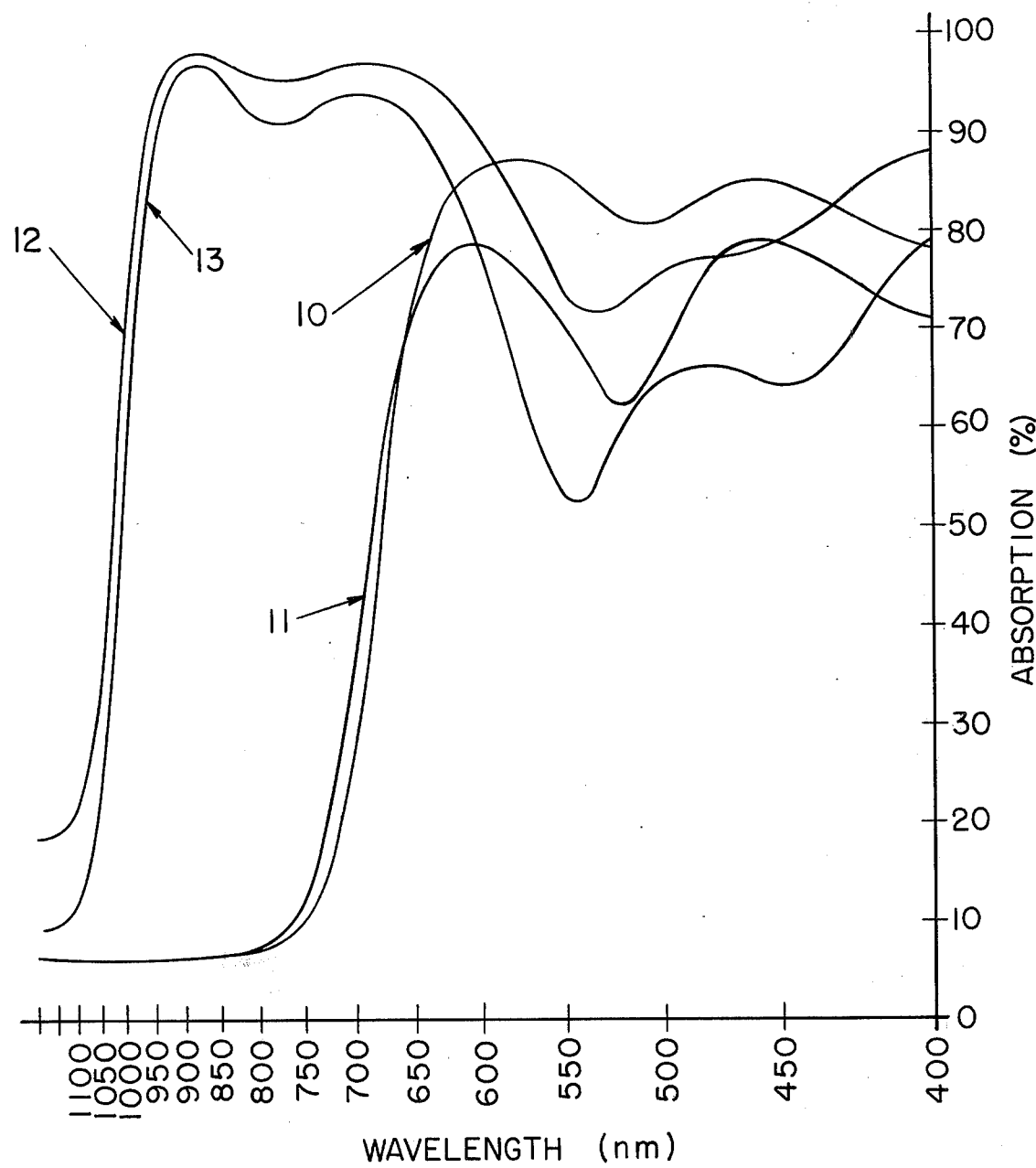
Figure 3:
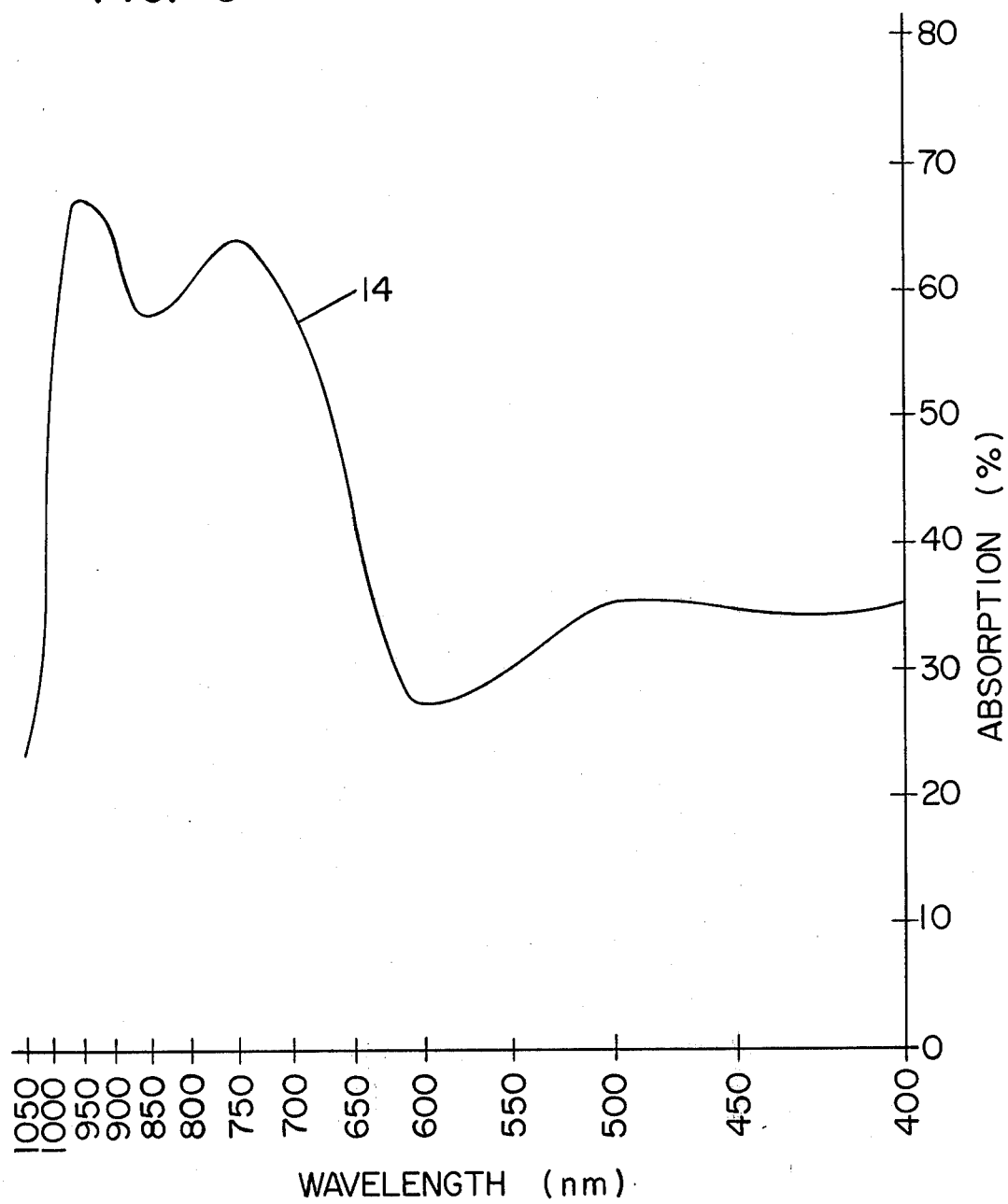

FIG. 2 is a comparative showing of the difference between reflectance of the colored form of the vinyl-containing compounds of this invention and the reflectance of similar compounds, but without the vinyl linkage, from the prior art. FIG. 3 is an additional example of the reflectance of di-vinyl compounds. The abscissa in those graphical showings represents wavelength on a reciprocal scale and the ordinate represents percent of incident light absorbed. Throughout the consideration of this invention, it should be kept in mind that light visible to the human eye exists from about 400 to 700 nanometers wavelength and machine readers and copiers exhibit a maximum sensitivity at about 830 nanometers. FIG. 2 indicates that those compounds of this invention are remarkably more absorbent of light in the machine reading range than are prior art compounds.

The curves of FIGS. 2 and 3 represent the light absorption characteristics of selected chromogenic compounds, in colored form, as reacted from solution on a paper coated with a phenolic resin. In FIG. 2, vinyl color formers of this invention are placed in comparative relation to compounds of the prior art having similar molecular structure or similar visible color; but without the vinyl element.

FIG. 2 is a comparison of the absorption spectra of 2'-anilino-3'-methyl-6'-diethylamino fluoran 10, and 2'-anilino-6'-diethylamino fluoran 11, with the absorption spectra of bis-3,3-[bis-2,2-(p-dimethylaminophenyl)ethyleno-1]-4,5,6,7-tetrachlorophthalide from Example 2, herein, 12 and bis-3,3-[bis-2,2-(p-diethylaminophenyl) ethyleno-1]-4,5,6,7-tetrachlorophthalide from Example 3, herein, 13. The prior at compounds of curves 10 and 11 are not structurally similar to the vinyl-containing compounds of curves 12 and 13 but these prior art compounds have been recognized as among the strongest color reactant absorbers in the wavelength range of about 400 to about 600 nm and higher. The vinyl-containing compounds of curves 12 and 13 are compared thereto as broad wavelength range absorbers.

FIG. 3 is an absorption spectrum of bis-3,3-[bis-2,2-(2-methyl-4-diethylaminophenyl)ethyleno-1]-4,5,6,7-tetrachlorophthalide 14 from Example 2, herein.

The spectral curves 12, 13, and 14 show strong absorption throughout the wavelength range of about 400 to about 1000 nm and especially above about 625 nm.

DETAILED DESCRIPTION OF THE INVENTION

It should be remembered that what is considered to be an essential element of the invention herein is the presence of two vinyl linkages in a colorless but colorable chromogenic material. At the present time, the chromogenic compounds of this invention enjoy extensive eligibility for use in pressure-sensitive and thermally-sensitive mark-forming systems. Pressure-sensitive mark-forming systems provide a marking system of disposing on and/or within sheet support material unreacted mark-forming components and a liquid solvent in which each of the mark-forming components is soluble, said liquid solvent being present in such form that it is maintained isolated by a pressure-rupturable barrier, from at least one of the mark-forming components until application of pressure causes a breach of the barrier in the area delineated by the pressure pattern. The mark-forming components are thereby brought into reactive contact, producing a distinctive mark.

The method of marking comprises providing a chromogenic compound selected from among the above-mentioned compounds and bringing such chromogenic compound into reactive contact, in areas where marking is desired, with an acidic color-activating substance to produce a dark-colored form of the chromogenic compound.

The acidic materials can be any compound within the definition of a Lewis acid, i.e., an electron acceptor. Preferably, acidic organic polymers, such as phenolic polymers, are employed as the acidic material. It is noted that the polymeric mark-forming components should have a common solubility with the chromogenic compound in at least one liquid solvent when the acid-reacting material is a phenolic or other organic acidic polymer. It is also noted that, in a single system, several chromogenic compounds can be used with the same or different polymeric materials. Several polymeric materials can be reactively contacted with a single chromogenic compound or with a mixture of chromogenic compounds.

The acidic polymeric material useful in this invention includes phenol polymers, phenol acetylene polymers, alkyl-phenolacetylene polymers, maleic acid-rosin resins, partially or wholly hydrolyzed styrene-maleic anhydride copolymers and ethylene-maleic anhydride copolymers, carboxy polymethylene and wholly or partially hydrolyzed vinyl methyl ether maleic anhydride copolymers and mixtures thereof.

When the acidic material is one of the aforementioned organic polymers, the liquid solvent chosen must be capable of dissolving the mark-forming components. The solvent can be volatile or non-volatile, and a single or multiple component solvent may be used which is wholly or partially volatile. Examples of volatile solvents useful in the aforedescribed basic chromogen-acidic polymer are toluene, petroleum distillate, perchloroethylene, and xylene. Examples of nonvolatile solvents are high-boiling point petroleum fractions, dioctyl adipate, biphenyls, diphenyl alkanes, and the like.

Generally, the solvent chosen should be capable of dissolving at least 0.3 percent, by weight, of the chromogenic compounds and at least about 3-5 percent, by weight, of the polymeric material. A further criterion of the solvent is that it must not interfere with the mark-forming reaction.

The support member, on which the components of the system are disposed, may comprise a single or dual sheet assembly. In the case where all components are disposed on a single sheet surface, the record material is referred to as a "self-contained" system. Where there must be a migration of the solvent, with or without mark-forming component, from one sheet to another, the record material is referred to as a "transfer" system. (Such a system can also be referred to as a "twofold" system, in that at least two sheets are required and each sheet includes a component, or components, essential to the mark-forming reaction.) Where a copious amount of the colored reaction product in liquid form is produced on a surface of one sheet, it can produce a mark by transfer to a second sheet as a colored mark.

The polymeric material can be dissolved in ink composition vehicles to form a printing "ink" of colorless character and, thus, can be used to spot-print a proposed record sheet unit sensitized for recording in a reaction-produced color in those areas by application of a solution of the chromogenic material. In the case of phenolic polymer, a printing ink can be made of up to 75 percent, by weight, of the phenolic polymeric material in a petroleum solvent to a viscosity suitable for printing purposes.

In the mark-forming system herein, the acidic markforming component(s) reacts with the chromogenic materials(s) to effect distinctive color formation or color change. In a multi-sheet system in which an acid organic polymer is employed, it is desirable to include other materials to supplement the reactants. For example, kaolin can be added to improve the transfer of the liquid and/or the dissolved materials between the sheets. In addition, other materials such as bentonite, attapulgite, talc, feldspar, halloysite, magnesium trisilicate, silica gel, pyrophyllite, zinc sulfide, calcium sulfate, calcium citrate, calcium phosphate, calcium fluoride, barium sulfate and tannic acid can be included. It should be noted that mineral materials such as kaolin, attapulgite, silica gel, silton clay, and the like can, also, be used alone or in combination with other materials as an acidic material coreactant.

Various methods known to the prior art and disclosed in the aforementioned U.S. Pat. No. 3,672,935 can be employed in coating compositions of the markforming materials into their supporting sheets. An example of the compositions which can be coated onto the surface of an underlying sheet of a two-sheet system to react with the chromogenic material on the underside of any overlying sheet is as follows:

| Coating Composition | Percent by Weight |
|---|---|
| Phenolic polymer mixture | 17 |
| Paper coating kaolin (white) | 57 |
| Calcium carbonate | 12 |
| Styrene butadiene latex | 4 |
| Ethylated starch | 8 |
| Gum arabic | 2 |
|  | 100 |

Thermally-sensitive mark-forming systems can also be prepared using the compounds of this invention.

The compounds of this invention can be prepared to be symmetrical or not as will be discussed in the examples which follow. Referring, again, to FIG. 1;—E can be the following:

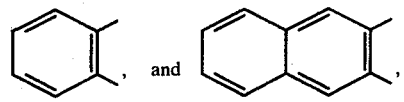

unsubstituted, and alkyl-, chloro-, dichloro-, trichloro-, tetrachloro-, bromo-, dibromo-, tribromo-, tetrabromo-, nitro-, and dialkylamino-substituted;

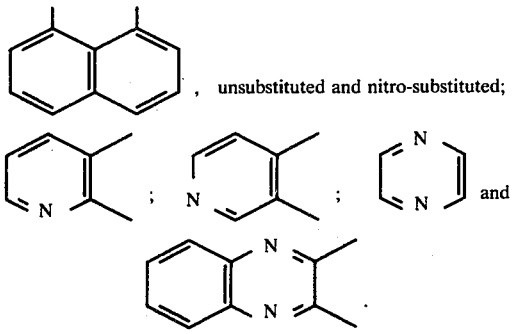, unsubstituted and nitro-substituted;

E can also be aromatic single anhydride residues such as result from homophthalic anhydride

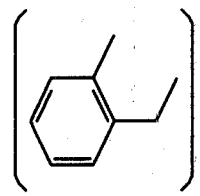

and biphenyl-6,2-dicarboxylic anhydride

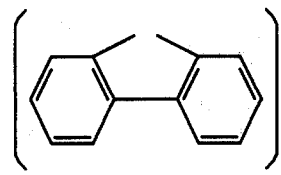

E can also be aliphatic anhydride residues such as result from keto-glutaric anhydrides.

X can be the following:

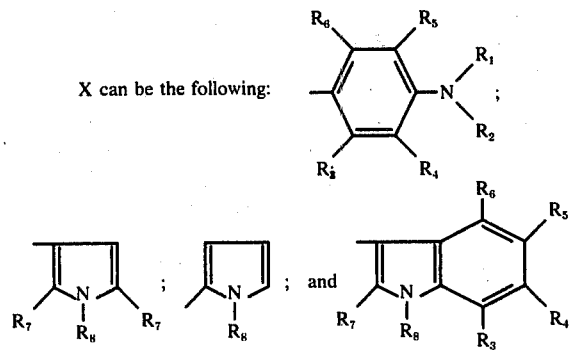

wherein $R_1$ and $R_2$ are hydrogen, alkyl, substituted phenyl, unsubstituted phenyl, benzyl, cycloalkyl, and acyl; $R_3$, $R_4$, $R_5$ and $R_6$ are hydrogen, alkyl, aryl, alkoxy, halo, aralkyl, dialkylamino, monoalkylamino, amino, acylamino, mercapto, and alkylthio; and $R_7$ and $R_8$ are hydrogen, phenyl and alkyl. $R_1$ and $R_2$ are not both phenyl.

Y can be any X and hydrogen.

Z can be hydrogen and methyl.

It should be understood that "alkyl" and any group requiring alkyl, such as "alkoxy" or "dialkylamino" means methyl, ethyl, propyl (including isopropyl), butyl (including isobutyl and tert-butyl), pentyl (including all five-carbon isomers), hexyl (including all six-carbon isomers), and the like having less than seven carbon atoms.

This invention is further illustrated by the following examples. The reactants and the proportions and other specific conditions are represented as being typical and should not be construed to limit the invention.

DESCRIPTION OF THE PREFERRED EMBODIMENTS

In the following examples, general procedures for preparing certain compounds of this invention are disclosed; and the procedures are followed by summaries of additional compounds prepared in similar manner. The summaries are not intended to be exhaustive and it must be remembered that the moieties, as previously defined, are all eligible for use in any combination in preparing the compounds.

EXAMPLE 1

Preparation of bis-3,3-[bis-2,2-(p-dimethylaminophenyl) ethyleno-1]phthalide.

With reference to the drawing in respect of this example and like examples which follow, the description of compound preparation does not specifically proceed through the keto-acid (II) although the keto-acid intermediate is exhibited in the drawing.

For ease in understanding, the Examples are summarized in listings of components: the (I) component, generally anhydride, and the (A) and (B) ethylene substrate components. The summarized listing of exemplary eligible compounds is believed to facilitate understanding of the invention.

Combining an appropriate anhydride with an appropriate ethylene base, results in a compound of this invention. This example will be given with details of reaction conditions and will be followed by an additional listing of exemplary compounds.

A mixture of 1.4 grams of phthalic anhydride (I) and 13.4 grams of bis-1,1-(p-dimethylaminophenyl)ethylene (A and B) is heated to reflux in 25 milliliters of acetic anhydride. The system is poured into ice and ammonia and extracted with toluene and the toluene is dried with sodium sulfate. The reaction product is recrystallized from heptane and toluene-petroleum ether and then is chromatographed. The product imparts a green color to paper coated with a phenolic resin or silton clay or a combination of the two. A reflectance spectrum of the green color has a peak 850 nanometers.

This example is also conducted using other anhydrides, such as 2,3-naphthalene dicarboxylic acid anhydride. The anhydrides of this Example are unsubstituted, and substituted with alkyl and dialkylamino groups; for example, 3 (or 4) ethyl, hexyl, or dibutylamino phthalic anhydride and 5 (or 6) ethyl, hexyl, or dibutylamino phthalic anhydride.

Example 1, Summarized.
(I) phthalic anhydride
    (A), (B) bis-1,1-(p-dimethylaminophenyl)ethylene
        green. absorption peak at 850 nanometers
  also (A), (B) bis-1,1-(p-diethylaminophenyl)ethylene
  also (A), (B) 2-methyl-bis-1,1-(p-dimethylaminophenyl)
        ethylene
  also (A), (B) 1-(p-dimethylaminophenyl)-1-(methoxyphenyl)
        ethylene
  also (A), (B) bis-1,1-(2-bromo-4-dihexylaminophenyl)
        ethylene
(I) 3-methylphthalic anhydride
    (A), (B) bis-1,1-(p-dimethylaminophenyl)ethylene
        green-blue. absorption peak at 830
        nanometers
  also (A), (B) 1-(p-dimethylaminophenyl)-1-(nitrophenyl)
        ethylene
(I) 4-methylphthalic anhydride
    (A), (B) bis-1,1-(p-dimethylaminophenyl)ethylene
        green-blue. absorption peak at 850
        nanometers
(I) 4-dimethylaminophthalic anhydride
    (A), (B) bis-1,1-(p-dimethylaminophenyl)ethylene
        green. absorption peak at 835 nanometers
  also (A), (B) bis-1,1-(p-dibutylaminophenyl)ethylene
  also (A), (B) p-dibutylaminophenylethylene
  also (I) 4-di-t-butylaminophthalic anhydride and
        4-hexylaminophthalic anhydride
  also (A), (B) bis-1,1-(pyrrol-3-yl)ethylene and bis-1,1-
        (pyrrol)-2-yl)ethylene
  also (A), (B) bis-1,1-(indol-3-yl)ethylene

EXAMPLE 2

Preparation of bis-3,3-[bis-2,2-(p-dimethylaminophenyl)ethyleno-1]-4,5,6,7-tetrachlorophthalide A mixture of 28.6 grams of tetrachloro-phthalic anhydride and 51.3 grams of 1,1-bis-(p-dimethylaminophenyl)ethylene are heated in 400 milliliters of acetic anhydride, at about 74° centigrade, for about one hour. The system is slowly cooled and the reaction product is filtered from the system and then dissolved in about 1200 milliliters of hot toluene. That toluene solution is cooled and 700 milliliters of petroleum either is added. After standing for about 12 hours, 56.5 grams of reaction product is separated by filtration and that reaction product exhibits a melting point of 247°–249° centigrade. A solution of the product imparts a dark green color to paper coated with a phenolic resin or silton clay or a combination of the two. A reflectance spectrum of the green color has peaks at 690 and 880 nanometers. The calculated analysis for $C_{44}H_{42}N_4O_2Cl_4$, the title compound, is C, 66.33%; H, 5.31%; N, 6.54%; and Cl, 17.80%. Found, on analysis: C, 66.53% H, 5.45%; N, 6.79% and Cl, 17.46%.

This example is also conducted using other anhydrides, such as 2, 3-naphthalene dicarboxylic and anhydride. The anhydrides of this Example are also mono-, di-, and tri-halo substituted rather than tetra-substituted; and bromine can be used rather than chlorine. It is understood, of course, that for different reactant component materials, the weight amounts must be adjusted to provide about one mol of (A) and (B) for each mol of (I).

Example 2, Summarized.
(I) 3,4,5,6-tetrachloro phthalic anhydride

-continued

| | |
|---|---|
| (A), (B) | bis-1,1-(p-dimethylaminophenyl)ethylene<br>green. absorption peaks at 690 and 880 nanometers |
| (A), (B) | bis-1,1-(2-methyl-4-dimethylaminophenyl)ethylene<br>neutral. absorption peak at 950 nanometers |
| (A), (B) | bis-1,1-(2-methyl-4-diethylaminophenyl)ethylene<br>neutral. absorption peaks at 925 and 740 nanometers |
| also (A), (B) | bis-1,1-(2-ethoxy-4-dimethylaminophenyl)ethylene |
| also (a), (B) | bis-1,1-(2-dimethylamino-4-diethylaminophenyl)ethylene |
| also (A), (B) | bis-1,1-(2-methylamino-4-diethylaminophenyl)ethylene |
| also (A), (B) | bis-1,1-(2-amino-4-dimethylaminophenyl)ethylene |
| also (A), (B) | bis-1,1-(2-acetamino-4-dimethylaminophenyl)ethylene |
| also (A), (B) | p-dimethylaminophenylethylene |
| (I) 3,4,5,6,-tetrabromophthalic anhydride | |
| (A), (B) | bis-1,1(p-dimethylaminophenyl)ethylene |
| (A), (B) | 2-methyl-bis-1,1-(p-dimethylaminophenyl)ethylene<br>green. absorption peaks at 640 nanometers |
| also (A), (B) | 1-(p-dimethylaminophenyl)-1-(pentoxyphenyl)ethylene |
| (I) 4-chlorophthalic anhydride | |
| (A), (B) | bis-1,1-(p-dimethylaminophenyl)ethylene<br>green. absorption peak at 875 nanometers |
| also (A), (B) | p-di-t-butylaminophenylethylene |
| (I) 2,3-naphthalene dicarboxylic acid anhydride | |
| (A), (B) | bis-1,1-(dimethylaminophenyl)ethylene<br>blue. absorption peaks at 625 and 840 nanometers |
| also (I) 3,4-dichlorophthalic anhydride | |
| also (A), (B) | p-di-t-butylaminophenylethylene |

EXAMPLE 3

3,4,5,6-tetrachlorophthalic anhydride (1 mol part) is mixed with bis-(1,1-p-diethylaminophenyl)methylcarbinol (2 mol parts) in acetic anhydride and reacted as previously disclosed. The reaction product is bis-3,3-[bis-2,2-(p-diethylaminophenyl)ethyleno-1]-4,5,6,7-tetrachlorophthalide. The calculated analysis for $C_{50}H_{58}N_4O_2Cl_4$, the reaction product, is C, 68.43%; H, 6.40% N, 6.14%; and Cl, 15.15%. Found, on analysis: C, 68.59%; H, 6.37%; N, 6.03%; and Cl, 15.38%. A solution of the material imparts a deep green color to paper coated with phenolic resin or silton clay of a combination of the two. A reflectance spectrum of the green color has peaks at 690 and 880 nanometers.

EXAMPLE 4

Preparation of bis-3,3-[bis-2,2-(p-dimethylaminophenyl) ethyleno-1]-4 (or 7)-nitrophthalide A mixture of 1.93 grams of 3-nitrophthalic anhydride and 5.3 grams of bis-1,1-(p-dimethylaminophenyl)ethylene is refluxed and reacted by the procedures previously disclosed; and the reaction product is isolated, as previously disclosed. The reaction product has a melting point of 208°–210° centigrade. A solution of the product imparts a deep green color to a paper coated with phenolic resin or silton clay or a combination of the two. A reflectance spectrum of the green color has absorption peaks at about 660 and 880 nanometers.

Example 4, Summarized.

| | |
|---|---|
| (I) 3-nitrophthalic anhydride | |
| (A), (B) | bis-1,1-(p-dimethylaminophenyl)ethylene<br>green. absorption peaks at 660 and 880 nanometers |
| (A), (B) | p-dimethylaminophenylethylene |
| (I) 4-nitrophthalic anhydride | |
| (A), (B) | bis-1,1-(p-dimethylaminophenyl)ethylene<br>black. absorption peak at 840 nanometers |
| also (A), (B) | 2-methyl-bis-1,1-(p-dimethylaminophenyl)ethylene |
| also (A), (B) | bis-1,1-(2-butoxy-4-dimethylaminophenyl)ethylene |
| (I) 4-nitro-1,8-naphthoic anhydride | |
| (A), (B) | bis-1,1-(p-dimethylaminophenyl)ethylene<br>green. absorption peak at 875 nanometers |
| (I) 1,8-naphthoic anhydride | |
| (A), (B) | bis-1,1-(p-dimethylaminophenyl)ethylene<br>green. absorption peak at 835 nanometers |

-continued

| | |
|---|---|
| (I) quinolinic anhydride (2,3-pyridine dicarboxylic acid anhydride) | |
| (A), (B) | bis-1,1-(p-dimethylaminophenyl)ethylene<br>green-blue. absorption peak at 875 nanometers |
| (I) 3,4-pyridinedicarboxylic acid anhydride | |
| (A), (B) | bis-1,1-(p-dimethylaminophenyl)ethylene<br>green. absorption peak at 860 nanometers |
| (I) 2,3-pyrazine dicarboxylic acid anhydride | |
| (A), (B) | bis-1,1-(p-dimethylaminophenyl)ethylene<br>purple. absorption peak at 700 nanometers |
| (I) quinoxalinic anhydride | |
| (A), (B) | bis-1,1-(p-dimethylaminophenyl)ethylene<br>brown. absorption peak at 700 nanometers |

EXAMPLE 5 preparation of chromogenic compounds based on homophthalic anhydride.

In this example, homophthalic anhydride (I) and bis-1,1-(dimethylaminophenyl)ethylene (A and B) are reacted together, in acetic anhydride, to yield the chromogenic compound (III) resulting from homophthalic anhydride with a disubstitution of the ethylene material. The colorless compound imparts a blue color to paper coated with a phenolic resin or silton clay or a combination of the two. A reflectance spectrum of the blue color has an absorption peak at 825 nanometers.

To prepare a chromogenic compound for this example, approximately 1 mol of each of (A) and (B) is required for each mol of (I). For instance, one mol of homophthalic anhydride (I) is reacted with two mols of any of the previously-disclosed vinyl compounds (A) and (B) such as bis-1,1-(p-diethylaminophenyl)ethylene, 2-methyl-bis-1,1-(p-dimethylaminophenyl)ethylene, and the like.

EXAMPLE 6

Preparation of chromogenic compounds based on biphenyl-6,2-dicarboxylic anhydride.

In this example, biphenyl-6,2-dicarboxylic anhydride (I) and bis-1,1-(dimethylaminophenyl)ethylene (A and B) are reacted together, in acetic anhydride, to yield the chromogenic compound (III) resulting from biphenyl-6,2′-dicarboxylic anhydride with a disubstitution of the ethylene material. The colorless compound imparts a blue color to paper coated with a phenolic resin or silton clay or a combination of the two. A reflectance spectrum of the blue color has an absorption peak at 825 namometers.

To prepare a chromogenic compound for this example, approximately 1 mol of each of (A) and (B) is required for each mole of (I). For instance, one mole of biphenyl-6,2'-dicarboxylic anhydride (I) is reacted with two mols of any of the previously-disclosed vinyl compounds (A) and (B) such as bis-1,1-(p-diethylaminophenyl)ethylene, 2-methyl-bis-1,1-(p-dimethylaminophenyl)ethylene, and the like.

EXAMPLE 7

Preparation of chromogenic compounds based on ketogluaric anhydride. Either of α-keto-glutaric anhydride or β-keto-glutaric anhydride are used.

In this example, keto-glutaric anhydride (I) and bis-1,1-(dimethylaminophenyl)ethylene (A and B) are reacted together, in acetic anhydride, to yield the chromogenic compound (III) resulting from ketoglutaric anhydride with a disubstitution of the ethylene material.

To prepare a chromogenic compound for this example, approximately 1 mol of each of (A) and (B) is required for each mol of (I). For instance, one mol of keto-glutaric anhydride (I) is reacted with two mols of any of the previously-disclosed vinyl compounds (A) and (B) such as bis-1,1-(p-diethylaminophenyl)ethylene, 2-methyl-bis-1,1-(p-dimethylaminophenyl)ethylene, and the like.

---

Example 7, Summarized.
(I) α-keto-glutaric anhydride
  (A), (B) bis-1,1-(dimethylaminophenyl)ethylene
    blue-green. absorption peaks at 650 and 870 nanometers
(I) β-keto-glutaric anhydride
  (A), (B) bis-1,1-(dimethylaminophenyl)ethylene
    green. absorption peaks at 650 and 870 nanometers

---

What is claimed is:
1. A compound represented by the formula:

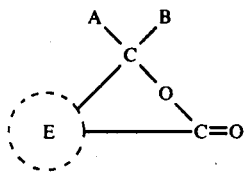

wherein E is

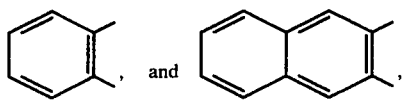

unsubstituted and alkyl-, chloro-, dichloro-, trichloro-, tetrachloro-, bromo-, dibromo-, tribromo-, tetrabromo-, nitro- and dialkylamino-substituted;

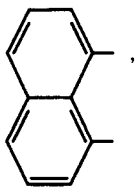

unsubstituted and nitro-substituted;

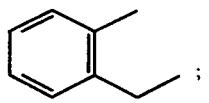

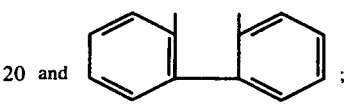

A and B are: 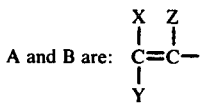

X is: 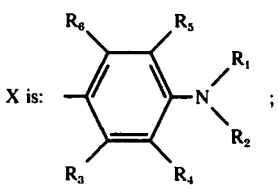

Y is: X or hydrogen;
Z is: hydrogen or methyl;
$R_1$ and $R_2$ are: hydrogen, alkyl, phenyl, and benzyl, and but $R_1$ and $R_2$ are not both phenyl;
$R_3$, $R_4$, $R_5$, and $R_6$ are: hydrogen, alkyl, phenyl, benzyl, alkoxy, halo, dialkylamino, monoalkylamino, amino, acetylamino; and
wherein alkyl, each occurrence, and alkoxy have one to six carbon atoms.

2. The compound of claim 1 wherein A and B are the same.

3. The compound of claim 2. wherein Y is:

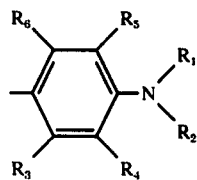

4. The compound of claim 2 wherein Y is hydrogen.
5. The compound of claim 3 wherein $R_1$ and $R_2$ are alkyl and $R_3$, $R_4$, $R_5$, $R_6$ and Z are hydrogen.
6. The compound of claim 3 wherein $R_1$, $R_2$ and $R_3$ are alkyl and $R_4$, $R_5$, $R_6$ and Z are hydrogen.
7. The compound of claim 4 wherein $R_1$ and $R_2$ are alkyl and $R_3$, $R_4$, $R_5$, $R_6$ and Z are hydrogen.

* * * * *

UNITED STATES PATENT AND TRADEMARK OFFICE
CERTIFICATE OF CORRECTION

PATENT NO. : 4,020,056

DATED : April 26, 1977

INVENTOR(S) : Sheldon Farber

It is certified that error appears in the above-identified patent and that said Letters Patent are hereby corrected as shown below:

Claim 1, column 12, line 39, after "halo," insert ---nitro,---.

Signed and Sealed this

Twenty-ninth Day of November 1977

[SEAL]

Attest:

RUTH C. MASON
Attesting Officer

LUTRELLE F. PARKER
Acting Commissioner of Patents and Trademarks